United States Patent [19]

Hannah

[11] 4,317,550
[45] Mar. 2, 1982

[54] APPARATUS FOR SUSPENDING A DRAINAGE BAG

[75] Inventor: Richard E. Hannah, Spring Grove, Ill.

[73] Assignee: Baxter Travenol Laboratories, Inc., Deerfield, Ill.

[21] Appl. No.: 76,021

[22] Filed: Sep. 17, 1979

[51] Int. Cl.³ .............................................. B65B 67/12
[52] U.S. Cl. ...................................................... 248/95
[58] Field of Search .............. 248/95, 99, 100, 101, 248/311.3, 318, 75; 128/275

[56] References Cited

U.S. PATENT DOCUMENTS

| | | | |
|---|---|---|---|
| Re. 23,858 | 8/1954 | Schneider | 150/12 |
| 2,769,474 | 11/1956 | Klotz | 150/12 |
| 3,039,506 | 6/1962 | Reiter | 150/12 |
| 3,090,968 | 5/1963 | Buono | 248/95 X |
| 3,192,979 | 7/1965 | Nolan | 150/8 |
| 3,217,770 | 11/1965 | Garth | 150/1 |
| 3,220,434 | 11/1965 | Garth | 248/100 X |
| 3,251,069 | 5/1966 | Clark | 248/75 X |
| 3,345,023 | 10/1967 | Scott et al. | 248/95 |
| 3,550,838 | 12/1970 | Hart | 229/54 |
| 3,568,965 | 3/1971 | Clark | 248/95 |
| 3,602,223 | 8/1971 | Engelsher | 128/275 |
| 3,650,272 | 3/1972 | Ericson | 128/275 |
| 4,019,707 | 4/1977 | Quinn | 248/95 |
| 4,027,842 | 6/1977 | Mittelman | 248/75 |
| 4,085,755 | 4/1978 | Burrage | 128/275 |
| 4,219,177 | 8/1980 | O'Day | 248/95 X |

*Primary Examiner*—William H. Schultz
*Attorney, Agent, or Firm*—Paul C. Flattery; John A. Caruso; Garrettson Ellis

[57] ABSTRACT

An apparatus for suspending a drainage bag from a patient's bed or other structure, so fluid can be drained from the patient into the bag. The apparatus includes a hanger to which the bag can be attached and a hook for securing the hanger with the attached bag to the bed rail. The hanger has a bag support spar, L-shaped arms depending therefrom, a clip on the free end of one of the arms, and a connector on the free end of the other arm, so that insertion of one of the arms into a slotted portion of the bag and then insertion of the connector into the clip secures the bag onto the hanger. The hook has an arm attachable to a tab on the hanger and other arms for securing the hook to the bed rail. The arms are constructed so that the hanger and hook can cooperate to suspend the bag in a vertical plane with respect to the ground. In one embodiment of the apparatus, the arm of the hook attachable to the hanger is semicircular. Irrespective of the orientation of the hook on the rail, the bag support spar of the hanger and the suspended bag lie in such a vertical plane because the tab of the hanger is free to rotate about the semicircular arm of the hook.

21 Claims, 5 Drawing Figures

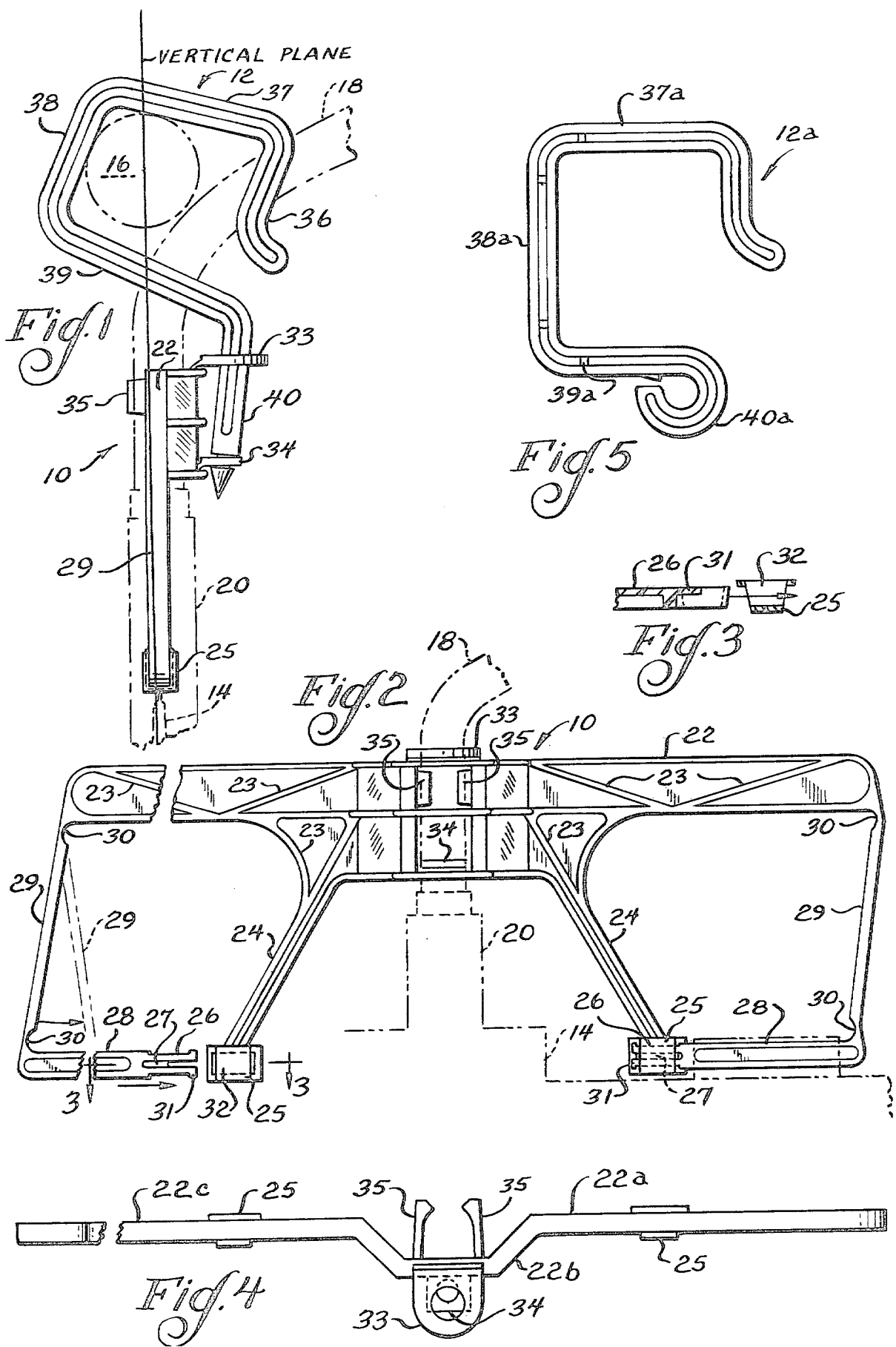

APPARATUS FOR SUSPENDING A DRAINAGE BAG

BACKGROUND OF THE INVENTION

This invention relates to an apparatus for suspending a drainage receptacle. More particularly, it relates to an apparatus for suspending a receptacle into which body fluids from a patient may be drained.

It is often necessary in a hospital to provide a drainage receptacle or bag in a convenient relation to a patient, so that body fluids can be drained from the patient into the receptacle. Such body fluids may include ones resulting from surgery, as well as urinary discharges. Because it is preferable to place the drainage bag below the patient for proper gravity flow, the most convenient place for hanging the bag is on the patient's bed; more particularly on the rail of the bed frame.

A known drainage bag includes tubing inserted in an inlet into which the patient's fluid is drained, a collecting portion, an outlet for removing the drained fluid from the bag, and a flow controller on the outlet, such as clamp. This type of drainage bag may also include components for measuring the amount of fluid drained, adding medicines or diagnostic reagents to the drained fluid, preventing flow of the drained fluid back to the patient, and withdrawing some of the drained fluid without opening the bag to the environment. Finally, such a bag also includes a hanger by which it is suspended from the patient's bed.

As is customary with hospital care, the patient, the patient's bed, and the bag are routinely manipulated for performing various tasks necessary to care for the patient. To accomplish these tasks, it is necessary that during these manipulations the hanger be constructed for keeping the bag in the desired orientation with respect to the ground. Generally, it is preferred that the bag hang in a vertical orientation to permit accurate measurement of its fluid content and, for example, avoid fluid backflow to the patient and that it hang in a horizontal orientation, where both sides of the bag are in the same horizontal plane and it is not bowed in or out. Second, the hanger should be capable of supporting the bag when it is filled with drained fluid. Further, it is preferable that the hanger be useful on both round and square bed rails and be easily affixable to a drainage bag, rather than being manufactured integrally with the bag or sealed thereto. In this last respect, in the attachment by the manufacturer of a handle to a drainage bag wherein the bag is found to be defective, if the handle is not an integral part of the bag it can be removed and placed on another bag, thereby saving in manufacturing costs.

Several hangers for suspending drainage bags are known in the prior art. One example of such a hanger is disclosed in U.S. Pat. No. 4,027,842 (Mittleman). This hanger does not have support by which it attaches to a drainage bag, but rather the bag has such a support integrally molded therein, which is disadvantageous for the reason specified above. U.S. Pat. No. 3,529,598 (Waldman) discloses a wire hanger for a drainage bag. It has been found that the incident of bag damage when a wire hanger is employed is greater than when a hanger of, for example, plastic is used. U.S. Pat. No. 3,650,272 (Erickson) discloses a "spring action" type hanger for suspending a drainage bag. Essentially, this hanger is Y-shaped with the branches of the Y being compressed to insert same into two pockets provided in the outermost, top portions of the bag. The spring action of the material of which the hanger is made is relied upon for holding the branches in the pockets and for suspending the bag. However, it has been found that when the bag is filled with drainage fluid, the fluid exerts the same compressing or downward force on the branches, which could either cause the uneven lowering of one side of the bag with respect to the other side of the bag or cause the bag to fall off the hanger, if the weight of the fluid is sufficient to snap one or both branches out of the pocket or pockets.

Thus, it is an object of the present invention to provide an apparatus for suspending a drainage bag wherein the handle of the apparatus is not integral, but easily assembled with the bag.

It is another object of the present invention to provide such a suspending apparatus which is useful on round or square bed rails or bed rails of various dimensions that are commonly found in hospitals.

It is another object of the present invention to provide such a suspending apparatus which will not permit the bag to accidentally fall off the apparatus or cause damage to the bag.

Finally, it is an important object of the present invention to provide a suspending apparatus which will maintain the bag in a vertical orientation with respect to the floor and which will maintain both sides of the bag in the same horizontal plane.

SUMMARY OF THE INVENTION

In accordance with the present invention, an apparatus is provided for suspending a drainage bag from a suspending structure, so body fluids can be drained from a patient into the bag. The apparatus includes a hanger to which the bag can be attached and a hook removably securable to the suspending structure and attachable to the hanger.

The hanger includes a bag support spar and means for holding the bag and preventing any unintended separation of it from the hanger, when fluids are drained into the bag. The preferred means includes an interlocking clip/connector assembly by which a portion of the bag is captured by the assembly to prevent the bag from falling off the hanger.

The hook includes at least one arm securable to the structure and another arm attachable to the hanger. The arms are constructed so that the hook and hanger can cooperate to suspend the bag in a vertical plane with respect to the ground. The arm of the hook attachable to the hanger is preferably constructed so that irrespective of the orientation of the hook on the rail, the bag support spar and the suspended bag lie in such a vertical plane.

BRIEF DESCRIPTION OF THE DRAWINGS

FIG. 1 is a side view of an apparatus for suspending a drainage bag of the present invention showing a drainage tube, a portion of the drainage bag, and a bed rail in dotted line.

FIG. 2 is a front view of the hanger of the apparatus of FIG. 1.

FIG. 3 is a cross-sectional view of a portion of the hanger taken along lines 3—3 of FIG. 2.

FIG. 4 is a top plan view of the hanger of FIG. 2.

FIG. 5 is a side view of another embodiment of a hook of the apparatus of the present invention.

DETAILED DESCRIPTION OF THE PREFERRED EMBODIMENTS

This drainage bag suspending apparatus generally includes a hanger 10 and a hook 12. As shown in FIG. 1, hanger 10 is attached to the drainage bag to be suspended, which is identified generally as 14, and hook 12 is affixed onto hanger 10. The hanger is then suspended over a bed rail 16. The bag and an inlet tubing 18, through which fluids are drained from the patient into the bag, are shown in the optimal use position, i.e. the bag, the hanger, and the bed rail all lie in the same vertical plane. By definition herein, "vertical plane" means a line, such as shown in FIG. 1, which extends through the named elements and would be perpendicular with respect to the ground if the bag were suspended in use. Generally, tubing 18 is attached to bag 14 by a connector 20.

Turning to FIG. 2, hanger 10, without hook 12, is shown. The hanger has an upper main support spar 22. This spar predominantly supports the drainage bag and for this purpose has ribs 23 trussed for maximum load bearing. The ribs are provided in a triangular orientation, which has been found to give greater resistance to deformation of support spar 22.

Integral with support spar 22, on each side of essentially the center of the spar, is an angled drop arm 24. As was mentioned above with respect to one of the prior art drainage bag hangers, it has been determined that upon filling of the drainage bag, forces are directed downwardly and towards the center of the filled bag. Therefore, to counteract such forces, arms 24 are angled outwardly. This gives the hanger increased resistance against bowing either in or out, which bowing would interfere with the optimal vertical orientation of the bag.

At the end of each drop arm 24 a snap-lock clip 25 is provided. The clip is essentially a female portion adapted to receive the insertion therein of a male connector 26. Each connector 26 has a webbed portion 27 to increase its thickness and rigidity.

Referring again to FIG. 2, each male connector 26 is an integral part of a bag bearing beam 28. The beam is attached to a swing arm 29, which extends upwardly and is integrally connected with an outermost end of main support spar 22. At the point where each swing arm 29 meets support spar 22 and each bag bearing beam 28 meets a swing arm 29, there is provided a hinge point 30. This hinge point allows for greater flexibility in manipulating the arm to insert the bag bearing beam through the appropriate opening or slot in the drainage bag for suspending the bag from hanger 10. The slot of the drainage bag through which beam 28 is inserted is shown in dotted line on the right side of FIG. 2. Again referring to FIG. 2, particularly each side of hanger 10, it should be noted that on the left side of the hanger, bag bearing beam 28 is shown prior to insertion of connector 26 into clip 25 and on the right side after insertion of the beam into the clip. By movement of swing arm 29 in the direction shown by the arrow to the point where the arm is shown in dotted line, connector 26 is inserted into clip 25, wherein fingers 31 of the connector are compressed. Viewing the right side of FIG. 2, once the connector has been inserted a sufficient distance in clip 25, fingers 31 clear a solid portion 32 of clip 25 and because of their resilient nature, they spring outwardly. Thus, the opening or slotted portion of drainage bag 14 overriding bag bearing beam 28 is now captured between the bag bearing beam connected to swing arm 29 and snap-lock clip 25. Without an active and intended action to reverse this process, it is highly unlikely that connector 26 could be separated from clip 25 to allow the slotted portion of the draining bag to fall off bag bearing beam 28. It should be noted, in looking at particularly the left side of FIG. 2, that prior to insertion of connector 26 into clip 25 swing arm 29 is angled outwardly approximately 8 degrees from a line perpendicular to spar 22. This arrangement is provided because when bag bearing beam 28 is moved in the direction of the arrow for insertion of connector 26 into clip 25, the beam normally moves out of a parallel relation with spar 22. Thus, when connector 26 is inserted in clip 25, as shown on the right side of FIG. 2, swing arm 29 is angled inwardly approximately the same number of degrees as it was previously angled outwardly, so that bag bearing beam 28 is parallel to support spar 22.

Turning now to the means by which hanger 10 and drainage bag 14 attached thereto are suspended from a bed rail, reference is made to FIG. 1. Hook 12 is affixed to hanger 10 by fold tabs 33 and 34. As shown, the tabs each have a load bearing surface connected by a thin, integral connecting portion to main spar 22 of hanger 10. As shown best in FIG. 2, provision is also made in main spar 22 for inlet tube supporting arms 35 that hold inlet tube 18 in the desired position within the hanger.

Hook 12 includes a front arm 36, a top arm 37, a rear arm 38, a bottom arm 39, and a hanger attaching arm 40, the latter of which is inserted through openings in tabs 33 and 34 for attachment of the hook to hanger 10. As shown in FIG. 1, when the hook is applied over bed rail 16, the rail sits in the corner between top arm 37 and rear arm 38. The dimensions of bottom arm 39 and hanger attaching arm 40 allow the hook to be attached to the hanger in a position forward of bed rail 16. Thus, the drainage bag actually hangs directly below the bed rail in a vertical orientation with the rail. Because main supporting spar 22 supports the weight of the drainage bag and the fluid drained into it, the spar is similarly constructed. Note in FIG. 4 that main supporting spar 22 has three portions, outside supporting portions 22a and 22c and an intermediate portion 22b, forward of the other portions of the spar. Therefore, not only does this construction eliminate any interference with inlet tube 18 positioned within tube supporting arms 35, but also allows the drainage bag, supporting spar 22, the portions of hook 12 resting on and below bed rail 16, and the bed rail itself to be in a common, vertical plane to insure the vertical orientation of the bag.

Another embodiment of a hook is shown in FIG. 5. In this embodiment top arm 37a is shorter in length than rear arm 38a. Further this hook, 12a, includes a semicircular attaching arm 40a instead of straight arm 40 of hook 12 of FIG. 1. It has been found that by elimination of lower tab 34 on main supporting spar 22 of hanger 10 and insertion of semicircular attaching arm 40a into upper tab 33 of spar 22, that no matter how hook 12a is positioned, the hanger attached thereto will hang in a vertical plane, such as shown in FIG. 1. Thus, hook 12a is particularly useful on square bed rails of various dimensions. For instance, if the top leg of the bed rail is 1¼ inches across, hook 12a may be used in the position shown in FIG. 5 with top arm 37a abutting the rail leg. However, if the top leg of the rail is 1¾ inches across, the hook may be turned 90 degrees so that rear arm 38a sits on this top leg, while the attached hanger and drainage bag still hang in a vertical plane adjacent the bed rail. It has also been found that similar to arm 40 of the FIG. 1 hook, attaching arm 40a of the FIG. 5 hook freely rotates in the hole in top tab 33. Therefore, it is possible to rotate the hook around into the same plane as the hanger for more compact packaging. Also, by the elimination of lower tab 34 and because of the flexibility of the connecting strip between tab 33 and main spar 22, any improper positioning of the hook on the bed rail will still not prevent the hanger and attached bag from being vertically oriented as shown in FIG. 1. Thus, the hook and hanger of the apparatus of the present invention cooperate to insure that the drainage bag being suspended hangs in a vertical orientation.

Other variations of the apparatus of the present invention are contemplated. For instance, clip 25 and connector 26 may be placed in other positions along bag beam 28 and arms 24 and 29. Clip 25 could be reversed with connector 26, so that the clip is an integral part of bearing beam 28 and the connector is an integral part of swing arm 24. The hook of the apparatus of the present invention could have a rounded corner between its top and rear arms to better conform to a round bed rail.

The hook and hanger of this apparatus are preferably constituted of a plastic material, such as polypropylene for the hanger and polyacetal for the hook, but may be made of other similar thermoplastic materials. These and other modifications and variations of the above described apparatus of the present invention are contemplated to be within the scope of this invention and not intended in any way as a limitation on this invention.

What is claimed is:

1. An apparatus useful for suspending from a structure a drainage bag into which body fluids can be drained, the apparatus comprising:
   a hanger to which a bag can be attached, the hanger comprising a bag support spar and means for holding the bag and preventing any unintended separation of it from the hanger; and
   a hook, the hook comprising at least one arm adapted for removable securement to a suspending structure and a second arm pivotally attached to the hanger,
   the hanger and hook each being independent members which cooperate to suspend the bag in a vertical plane with respect to the ground when the hook is secured to a suspending structure, the hanger is attached to the hook, and a bag is attached to the hanger,
   the means for holding the bag including two pairs of arms depending from the support spar, and retention means extending from one of the arms of each pair toward the other of said arms of the pair, said retention means being capable of locking to said other arm, whereby a portion of a bag may be captured along said retention means of each pair of arms and locked in place, each pair of arms being spaced on opposite sides of the center of said spar to permit the hanging of a bag having a central entry port.

2. The apparatus of claim 1 wherein the spar comprises an intermediate portion and an outside supporting portion on each side of the intermediate portion, the means includes a bag retaining assembly integral with each outside supporting portion, and the intermediate portion is forward of the outside supporting portions.

3. The apparatus of claim 2 wherein, with respect to each assembly, one arm of each pair depends from the spar adjacent a point where the intermediate portion and one of the outside supporting portions merge and is angled outwardly towards the other arm, which depends from the outermost extremity of that one of the outside supporting portions of the spar.

4. The apparatus of claim 1 wherein the hanger further comprises at least one tab having load bearing surface portions defining a hole through which the second arm of the hook can be inserted.

5. The apparatus of claim 4 wherein the spar comprises an an intermediate portion and an outside supporting portion on each side of the intermediate portion, the intermediate portion is forward of the outside supporting portions and the tab is connected to the forward facing side of the intermediate portion and extending outwardly therefrom.

6. The apparatus of claim 4 wherein the tab has a thin flexible portion by which it is connected with the hanger.

7. The apparatus of claim 4 wherein the second arm of the hook, by which the hook is attached to the hanger, is generally forward of the part of the arm of the hook which rests on the structure to secure the hook to the structure, so that this part, the structure, the bag supporting portions of the spar, and the suspended bag are in a vertical plane.

8. The apparatus of claim 4 wherein the second arm of the hook, by which the hook is attached to the hanger, is substantially semicircular, so that irrespective of the orientation of the hook with regard to the hanger, at least the bag supporting portions of the spar and the suspended bag are in a vertical plane.

9. The apparatus of claim 1 in which the inner arm of each pair is outwardly angled.

10. The apparatus of claim 9 in which the outer arms of each pair exhibit lines of flexing weakness to permit pivotal motion toward and away from the inner arm of the pair.

11. The apparatus of claim 10 in which said outer arms extend inwardly when in locked relation with the inner arms.

12. The apparatus of claim 1 in which at least one arm of each pair carries pivotal flex means to permit the arm to pivot into and out of locking relationship with the other arm of the pair.

13. The apparatus of claim 1 in which flexible tab means are carried at the center of said hanger, said hook being pivotally mounted with its second arm defining a substantially semicircular loop and extending through a perforation in said tab, whereby said hook may be folded flat against the hanger by rotation of the flexible tab means to a position substantially 90° from its normal hanging position.

14. The apparatus of claim 1 in which one arm of each pair carries a horizontally extending bag-bearing beam proportioned for locking connection with a clip on the other of said arms of the pair, and flex means permitting the horizontally extending bag-bearing beam to rotationally flex relative to the arm upon which it is carried.

15. An apparatus useful for suspending a drainage bag into which body fluids can be drained, the apparatus comprising:
   a hanger to which a bag can be attached, the hanger comprising a bag support spar and means for holding the bag for preventing any unintended separation of it from the hanger when the bag is filled with fluid, and a hook, the hook comprising at least one arm adapted for removable securement to a suspending structure and a second arm pivotally attached to the hanger, said hanger and hook each being independent members which cooperate to suspend the bag in a vertical plane with respect to the ground when the hook is secured to a suspending structure, the hanger is attached to the hook, and a bag is attached to the hanger;

said means for holding the bag including bag retaining assemblies, the assemblies each comprising a pair of arms depending from the support spar, a clip on the free end of one of the arms, and a connector on the free end of the other of the arms, whereby a portion of the bag is attached to the assembly by which the bag is suspended from the hanger, captured between the arms when the connector is inserted in the clip, said spar comprising an intermediate portion and an outside supporting portion on each side of the intermediate portion, the bag holding means including a bag retaining assembly integral with each outside supporting portion, and the intermediate portion being positioned forward of the outside supporting portions.

16. The apparatus of claim 15 wherein, with respect to each assembly, one of the arms depends from the spar adjacent the point where the intermediate portion and one of the outside supporting portions merge, said one arm being angled outwardly toward the other arm, said other arm depending from the outermost extremity of an outside supporting portion of the spar.

17. An apparatus useful for suspending from a structure a drainage bag into which body fluids can be drained, the apparatus comprising:

a hanger to which a bag can be attached, the hanger comprising a bag support spar and means for holding the bag including two pairs of arms depending from the support spar, retention means extending from one of the arms of each pair toward the other of said arms of the pair, said retention means being capable of locking to said other arm, whereby a portion of the bag may be captured along said retention means of each pair of arms and locked in place, each pair of arms being spaced on opposite sides of the center of said spar to permit the hanging of a bag having a central entry port, the inner arm of each pair being angled outwardly and the outer arms of each pair exhibiting lines of flexing weakness to permit pivotal motion of the outer arms toward and away from the inner arm of the pair;

a hook, the hook comprising at least one arm adapted for removable securement to a suspending structure and a second arm pivotally attached to the hanger, the hanger and hook each being independent members which cooperate to suspend the bag in a vertical plane with respect to the ground.

18. The apparatus of claim 18 in which said outer arms extend inwardly when in locked relation with the inner arms.

19. The apparatus of claim 18 in which flexible tab means are carried at the center of said hanger, said hook being pivotally mounted with its second arm defining a substantially semicircular loop and extending through a perforation in said tab, whereby said hook may be folded flat against the hanger by rotation of the flexible tab means to a position substantially 90° from its normal hanging position.

20. The apparatus of claim 19 in which said retention means extending from one of the arms of each pair is a horizontally extending bag-bearing beam for locking connection with a clip on the other of said arms of the pair.

21. The apparatus of claim 20 in which flex means are provided permitting the horizontally extending bag-bearing beam to rotationally flex relative to the arm upon which it is carried.

* * * * *